United States Patent
Van Zijl et al.

(12) United States Patent (10) Patent No.: US 7,894,875 B2
(45) Date of Patent: Feb. 22, 2011

(54) QUANTIFYING BLOOD VOLUME USING MAGNETIZATION TRANSFER MAGNETIC RESONANCE IMAGING

(76) Inventors: Peter C. M. Van Zijl, 7712 Millstone Ct., Ellicott City, MD (US) 21043; Jinyuan Zhou, 5 Quiet Stream Ct., Apt. E, Timonium, MD (US) 21093

( * ) Notice: Subject to any disclaimer, the term of this patent is extended or adjusted under 35 U.S.C. 154(b) by 1120 days.

(21) Appl. No.: 11/628,089

(22) PCT Filed: Jun. 1, 2005

(86) PCT No.: PCT/US2005/019339

§ 371 (c)(1),
(2), (4) Date: Nov. 29, 2006

(87) PCT Pub. No.: WO2006/004596

PCT Pub. Date: Jan. 12, 2006

(65) Prior Publication Data

US 2008/0021306 A1    Jan. 24, 2008

Related U.S. Application Data

(60) Provisional application No. 60/575,988, filed on Jun. 1, 2004.

(51) Int. Cl.
*A61B 5/055* (2006.01)
(52) U.S. Cl. .......... 600/419; 600/410; 600/420
(58) Field of Classification Search ........ 600/410, 600/419, 420; 324/307, 309
See application file for complete search history.

(56) References Cited

U.S. PATENT DOCUMENTS

| | | | |
|---|---|---|---|
| 5,050,609 A | 9/1991 | Balaban et al. | 128/653 |
| 5,627,468 A | 5/1997 | Kojima et al. | 324/307 |
| 5,655,531 A | 8/1997 | Nishimura et al. | 128/653.2 |
| 2002/0169372 A1 | 11/2002 | Miyazaki | 600/410 |
| 2002/0198449 A1 | 12/2002 | Baumgardner et al. | 600/420 |
| 2003/0030435 A1 | 2/2003 | Venkatesan et al. | 324/306 |

(Continued)

FOREIGN PATENT DOCUMENTS

WO    WO 2004/021028 A1    3/2004

OTHER PUBLICATIONS

Ropele et al. "A Comparison of magnetization Transfer Ratio, magnetization transfer Rate, and the Native Relaxation Time of Water Protons Related to Relapsing-remitting multiple Sclerosis", American Journal of Neuroradiology vol. 21, pp. 1885-1891, Nov./Dec. 2000.*

(Continued)

*Primary Examiner*—Ruth S Smith
*Assistant Examiner*—Joseph Santos
(74) *Attorney, Agent, or Firm*—Fay Sharpe LLP (57) ABSTRACT

A magnetic resonance method for imaging blood volume in parenchyma via magnetic transfer (MT) includes: determining a MT effect of parenchyma; determining a MT effect of tissue; and quantifying the parenchymal blood volume using the difference between the MT effect of parenchyma and the MT effect of tissue. In one embodiment, the parenchymal blood volume is quantified through the following: $MTR_{par} = MTR_{tissue}(1 - BV/V_{par})$, where $MTR_{par}$ is the magnetization transfer ratio of parenchyma, $MTR_{tissue}$ is the magnetization transfer ratio of tissue, BV is the blood volume, and $V_{par}$ is a total parenchymal water volume.

29 Claims, 9 Drawing Sheets

U.S. PATENT DOCUMENTS

2004/0059213 A1 3/2004 Kassai et al. ............... 600/410

OTHER PUBLICATIONS

Lu, et al., "Multiple Acquisitions With Global Inversion Cycling (MAGIC): A Multislice Technique For Vascular-Space-Occupancy Dependent fMRI", Mag. Res. in Medicine 51: 9-15 (2004).

Zhou, et al., "The Interaction Between Magnetization Transfer and Blood-Oxygen-Level-Dependent Effects", Mag. Res. in Medicine 53:356-366 (2005).

Kim, et al., "Effectof Magnetization Transfer on Quantification of CBF", Proc. Intl. Soc. Mag. Reson. Med. 11 (2004).

Song, et al., "The Effect of Off-Resonance Radiofrequency Pulse Saturation of fMRI Contrast", NMR in Biomed. 10, 208-215 (1997).

Zhang, et al., "The Effect of Magnetization Transfer on Functional MRI Signals", MRM 38:187-192 (1997).

Rosen, et al., "Contrast Agents and Cerebral Hemodynamics", Mag. Res. in Med. 19, 285-292 (1991).

Belliveau, et al., "Functional Mapping of the Human Visual Cortex by Magnetic Resonance Imaging" Science, vol. 254, 716-719 (1991).

Rosen, et al., "Future Uses of MR Imaging Agents", J. of Computer Assist. Tomography, 17 (Suppl. 1):S36-S42 (1993).

Sorensen, et al., "Contrast Agents in Functional MR Imaging", J. Magn. Reson. Imaging, 1997, 7:47-55.

Mandeville, et al., "Dynamic Functional Imaging of Relative Cerebral Blood Volume During Rat Forepaw Stimulation", MRM 39: 615-624 (1998).

Van Bruggen, et al, "High-Resolution Functional Magnetic Resonance Imaging of the Rat Brain: Mapping Changes in Cerebral Blood Volume Using Iron Oxide Contrast Media", J. of Cerebral Blood Flow & Metabolism 18: 1178-1183 (1998).

Sakoh, et al., "Cerebral Blood Flow and Blood Volume Measured by Magnetic Resonance Imaging Bolus Tracking After Acute Stroke in Pigs. Comparison With [$^{15}$O]H$_2$O Positron Emission Tomography", Stroke 31:1958-1964.

Phelps, et al., "Validation of Tomographic Measurement of Cerebral Blood Volume with C-11-Labeled Carboxyhemoglobin", J. Nucl. Med 20:328-334 (1979).

Duong, et al., "In Vivo MR Measurements of Regional Arterial and Venous Blood Volume Fractions in Intact Rat Brain", Magn. Reson. Med 43:393-402 (2000).

Lee, et al., "Relative Changes of Cerebral Arterial and Venous Blood Volumes During Increased Cerebral Blood Flow: Implications for BOLD fMRI", Mag. Reson. Med. 45:791-800 (2001).

Ito, et al., "Changes in Human Regional Cerebral Blood Flow and Cerebral Blood Volume During Visual Stimulation Measured by Positron Emission Tomography", J. of Cerebral Blood Flow and Metabolism 21:608-612 (2001).

Jones, et al., "Concurrent Optical Imaging Spectroscopy and Laser-Doppler Flowmetry: The Relationship Between Blood Flow, Oxygenation, and Volume in Rodent Barrel Cortex", NeuroImage 13: 1002-1015 (2001).

Ogawa, et al., "Brain Magnetic Resonance Imaging with Contrast Dependent on Blood Oxygenation", Proc. Natl. Acad. Sci. USA 87:9868-9872 (1990).

Ogawa, et al., "Intrinsic Signal Changes Accompanying Sensory Stimulation: Functional Brain Mapping with Magnetic Resonance Imaging", Proc. Natl. Acad. Sci. USA 89:5951-5955 (1992).

Kwong, et al., "Dynamic Magnetic Resonance Imaging of Human Brain Activity During Primary Sensory Stimulation", Proc. Natl. Acad. Sci. USA 89:5675-5679 (1992).

Van Zijl, et al., "Quantitative Assessment of Blood Flow, Blood Volume and Blood Oxygenation Effects in Functional Magnetic Resonance Imaging", Nature Med 4:159-167 (1998).

Ulatowski, et al., "In Vivo Determination of Absolute Cerebral Blood Volume Using Hemoglobin As a Natural Contrast Agent: An MRI Study Using Altered Arterial Carbon Dioxide Tension", J. Cerebl Blood Flow Metab. 19:809-817 (1999).

Lu, et al., "Functional Magnetic Resonance Imaging Based on Changes in Vascular Space Occupancy", Magn. Res. Med 50:263-274 (2003).

Wright, et al., "Estimating Oxygen Saturation of Blood in Vivo with MR Imaging at 1.5T", J. Magn. Reson. Imag. 1:275-283 (1991).

Meyer, et al, "NMR Relaxation Rates and Blood Oxygenation Level", MRM 34:234-241 (1995).

Silvennoinen, et al., "Comparison of the Dependence of Blood $R_2$ and $R^*_2$ on Oxygen Saturation At 1.5 and 4.7 Tesla", Magn Reson Med 49:47-60 (2003).

Wolff, et al., "Magnetization Transfer Contrast (MTC) and Tissue Water Proton Relaxation in Vivo", Mag. Reson. Med. 10:135-144 (1989).

Balaban, et al., "Magnetization Transfer Contrast in Magnetic Resonance Imaging", Magn. Reson. Q 8:116-137 (1992).

Henkelman, et al, "Magnetization Transfer in MRI: A Review", NMR Biomed. 14:57-64 (2001).

Edelman, et al., "Improved Time-of-Flight MR Angiography of the Brain with Magnetization Transfer Contrast", Radiology 184:395-399 (1992).

Pike, et al., "Magnetization Transfer Time-of-Flight Magnetic Resonance Angiography", Mag. Reson. Med. 25:372-379 (1992).

Atkinson, et al., "Magnetic Resonance Angiography", Mag. Reson. Q, 10:149-172 (1994).

* cited by examiner

QUANTIFYING BLOOD VOLUME USING MAGNETIZATION TRANSFER MAGNETIC RESONANCE IMAGING

CROSS REFERENCE TO RELATED PATENTS AND APPLICATIONS

This application is a National Stage of International Application No. PCT/US05/19339 filed Jun. 1, 2005, which claims the benefit of U.S. Provisional Patent Application Ser. No. 60/575,988, filed on Jun. 1, 2004, and entitled "QUANTIFYING BLOOD VOLUME USING MAGNETIZATION TRANSFER MAGNETIC RESONANCE IMAGING," the entirety of which is incorporated herein by reference.

GOVERNMENT LICENSE RIGHTS

The U.S. Government has a paid-up license in this invention and the right in limited circumstances to require the patent owner to license others on reasonable terms as provided for by the terms of Contract/Grant Nos. NIH/NIBIB: EB002666; NIH/NIBIB: EB002634; and NIH/NIBIB: EB 04130.

BACKGROUND

The following relates to non-invasive techniques for quantifying blood volume. It finds particular application to quantifying microvascular blood volume through magnetic resonance imaging techniques.

Conventionally, invasive and non-invasive techniques are used to measure blood volume. Invasive techniques include positron emission tomography (PET), dynamic contrast magnetic resonance imaging (DC MRI), dynamic susceptibility contrast MRI (DSC MRI), near infrared spectroscopy (NIRS), and optical imaging. Typical PET techniques are based on the administration of radioactive compounds, for example, through an arterial line or inhalation of C-11 or O-15 carbon monoxide. MRI techniques usually employ exogenous contrast agents (e.g., Gd-DTPA, MION) and a venous catheter for contrast agent injection/infusion.

One non-invasive approach uses nulling of the blood signal to measure blood volume changes. This approach is referred to as vascular space occupany (VASO). The VASO technique leverages the difference in longitudinal relaxation time $T_1$ between blood and tissue and separates out the blood contributions to the parenchymal MR signal using a suitable inversion recovery time. Another non-invasive approach is blood-oxygen-level-dependent (BOLD) functional MRI (fMRI). BOLD fMRI depends on blood volume, blood relaxation times $R_2$, etc., and could, in principle, be used to determine blood volume. For instance, BOLD fMRI potentially can be used to measure blood volume through established procedures involving hypoxia, hypercapnia, etc. However, the BOLD effect depends on many physiological parameters that render the derived blood volume changes sensitive to many inherent assumptions and calibrations.

In view of the aforementioned deficiencies of conventional blood volume quantifying techniques, there is an unresolved need for improved non-invasive blood volume quantifying techniques.

BRIEF SUMMARY

A magnetic resonance method for imaging blood volume in parenchyma via a magnetization transfer (MT) effect includes determining a MT effect of parenchyma, consisting of pure tissue and microvascular blood, determining a MT effect of pure tissue, and quantifying parenchymal blood volume based on a difference between the MT effect of parenchyma and the MT effect of tissue.

One advantage includes determining blood volume.

Another advantage resides in determining parenchymal blood volume through magnetization transfer ratios (MTRs).

Another advantage resides in determining blood volume through MRI scans.

Another advantage is computing blood volume without using a contrast agent.

Another advantage is computing blood volume with limited assumptions.

Another advantage resides in quantitatively and non-invasively measuring blood volume.

Still further advantages will become apparent to those of ordinary skill in the art upon reading and understanding the detailed description of the preferred embodiments.

BRIEF DESCRIPTION OF THE DRAWINGS

The drawings are only for purposes of illustrating working embodiments and are not to be construed as limiting the invention.

DETAILED DESCRIPTION OF THE PREFERRED EMBODIMENTS

Figure 1:
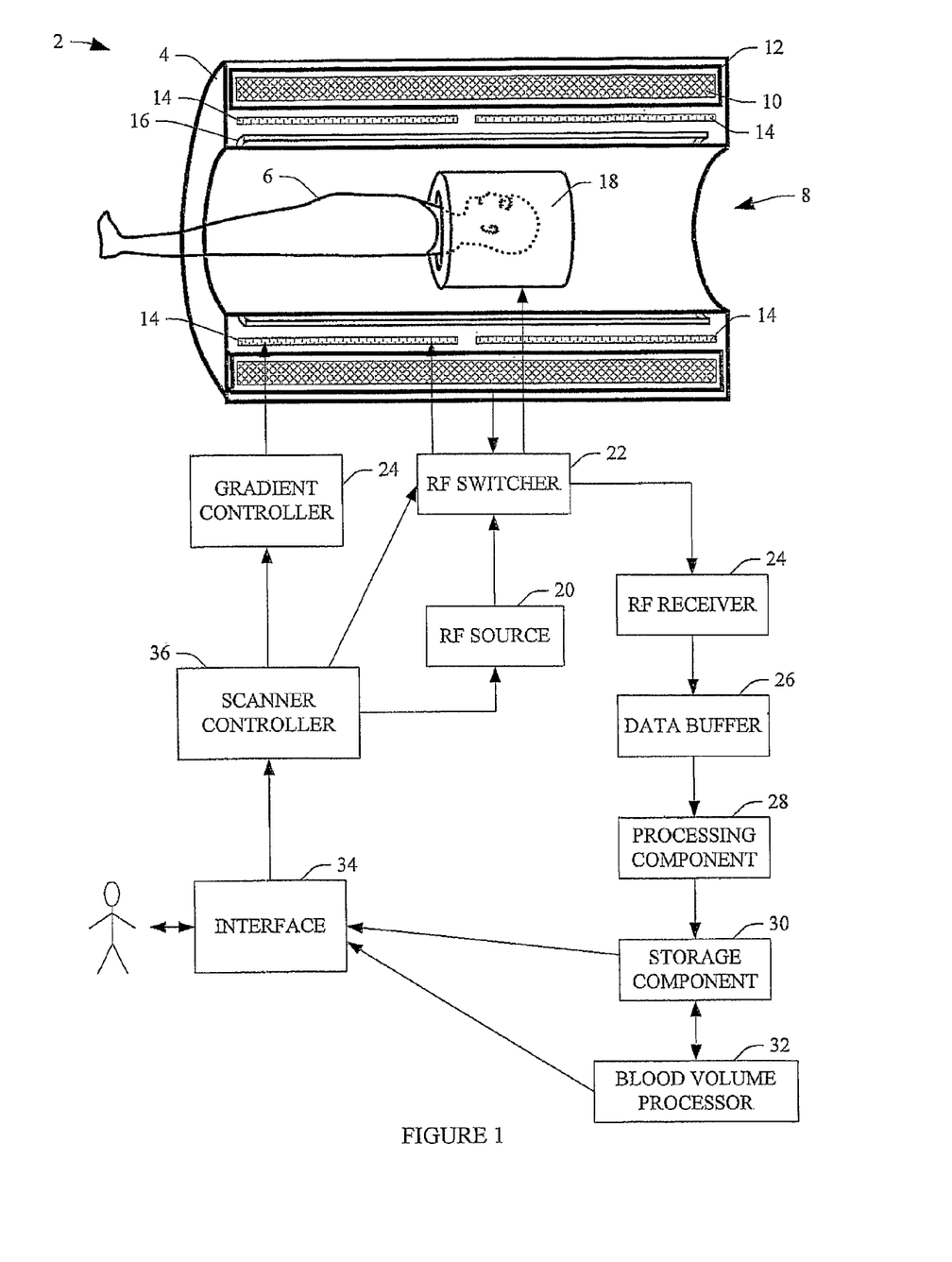
FIG. 1 illustrates an exemplary magnetic resonance imaging scanner used to facilitate determining blood volume through magnetization transfer (MT) properties.

FIG. 1 illustrates a magnetic resonance imaging (MRI) scanner 2 used to facilitate determining blood volume through magnetization transfer (MT) properties. An absolute blood volume map can be obtained by combining conventional MRI scanning techniques and using large MT-based reduction of tissue signal with respect to blood signal for non-invasive determination of absolute and relative blood volume effects in all tissues.

The scanner 2 includes a scanner housing 4. A subject 6 (or other object) is at least partially disposed within a bore 8 of the housing 4 for one or more scanning procedures. A magnet 10 resides in the scanner housing 4. Typically, the magnet 10 is a persistent superconducting magnet surrounded by cryoshrouding 12. However, other known magnets can be employed. The magnet 10 generates a magnetic field ($B_0$) in the subject 6. Typical magnetic fields strengths are about 0.5 Tesla, 1.0 Tesla, 1.5 Tesla, 3 Tesla or higher (e.g., about 7 Tesla).

Magnetic field gradient coils 14 are arranged in and/or on the housing 4 to superimpose selected magnetic field gradients on $B_0$. The magnetic field gradient coils 14 typically include coils for producing orthogonal magnetic field gradients. For instance, these coils can generate gradients in a Cartesian plane, such as x, y and/or z gradients. One or more radio frequency (RF) coils are located in the bore of the scanner 2 to inject radio frequency excitation pulses ($B_1$) and measure magnetic resonance signals. As depicted, a full body RF coil 16 surrounds the portion of the subject 6 in the bore 10 and, optionally, a head RF coil 18 surrounds a head of the subject 6.

For data acquisition, a RF source 20 is coupled to the coils 16 and/or 18 through a RF switcher 22 to inject radio frequency excitation pulses into the imaging region. The RF switcher 22 receives MR signals from the subject 6 through MR signal sensing circuitry (not shown). A magnetic field gradient controller 24 operates the magnetic field gradient coils 14 to spatially encode the magnetic resonances. For example, a one-dimensional magnetic field gradient applied during RF excitation produces slice-selective excitation; magnetic field gradients applied between excitation and readout of magnetic resonances provide phase encoding; and magnetic field gradients applied during readout of magnetic resonances provide frequency encoding. The magnetic resonance imaging pulse sequences can be configured to produce Cartesian, radial, spiral, or other spatial encodings.

During a readout phase, the switcher 22 disconnects the RF source 20 from the coils 16 and/or 18 and connects a RF receiver 24 to the coils 16 and/or 18 to acquire spatially encoded magnetic resonances from the subject 6. The acquired magnetic resonances are stored in a data buffer 26 and subsequently processed by a processing component 28 to produce one or more images. Conventional images without MT are stored in storage component 30. Images with an MT preparatory sequence are stored in a storage component 30. Optionally, additional images with different levels of MT or different tissue/blood relative contributions can also be generated and stored. The processing component 28 employs various reconstruction algorithms that suitably decode the spatially encoded magnetic resonances. For example, if Cartesian encoding is employed, a two or three dimensional fast Fourier transform (FFT) reconstruction algorithm typically is used.

A blood volume processor 32 analyzes the corresponding voxels of the images with different MT encoding or different relative tissue/blood contributions and generates a blood volume value for each. Collectively, the blood volume values for each voxel constitute a blood volume image. The reconstructed images are displayed on a user interface 34 or another display device, printed, communicated over a network (e.g., the Internet, a local area network (LAN) . . . ), stored within a storage medium, and/or otherwise used. The user interface 34 also allows an operator to control the magnetic resonance imaging scanner 2 through conveying instructions to a scanner controller 36.

The MRI scanner 2 is also used to facilitate determining blood volume from data collected through MRI scans of the subject 6. For such procedures, the user configures MRI scanning protocols to induce a magnetization transfer (MT) effect. This configuration includes setting up the scanner 2 to apply preparatory RF pulses during scanning of the subject 6. The user configures the scanning procedures through the user interface 34 by selecting options and inputting parameter values or loading default parameters.

As a result of the pulses, MR signals are reduced. In particular, the MR signal associated with relatively solid components of the subject 6 is reduced by the MT pulses more than the MR signal associated with less solid components of the subject 6. As a consequence, the MT effect associated with tissue is much greater than the MT effect associated with blood. The volume of microvascular blood is derived from measurements of the MT effect on tissue and blood together and the MT effect on tissue alone. The MT effect on both blood and tissue can be obtained through conventional MRI scanning techniques. The MT effect on tissue only can be obtained through blood-nulling techniques, such as the VASO approach. The MT effect can be varied by changing the number of pulses, the length and/or strength of the pulses, or the offset of the pulses.

The user initiates scanning by sending control signals to the scanner controller 36 via the user interface 34. The subject 6 is scanned and data is collected as summarized above and described in greater detail below. The blood volume processor 32 receives and processes the MR signals. In resultant images, each voxel is associated with a grey scale that represents its blood content.

In one instance, the blood volume processor 32 determines blood volume based on the MT effect of parenchyma and tissue. With this approach, the processor component 32 determines MT properties of parenchyma through a parenchymal MR signal captured in the presence of off-resonance RF irradiation and a parenchymal MR signal captured absent of off-resonance RF irradiation. The blood volume processor 32 determines MT properties of tissue through a tissue MR signal captured in the presence of off-resonance RF irradiation and a tissue MR signal captured absent of off-resonance RF irradiation. The blood volume processor 32 quantifies parenchymal blood volume through the difference between the MT properties of parenchyma and the MT properties of tissue. Additionally or alternatively, the processing component 32 determines a blood volume effect in parenchyma and a blood volume effect in tissue, and quantifies an effect of blood volume change therefrom. The resulting blood volume and/or the effect of blood volume change is displayed to the user on the user interface 34, stored in the storage component 30, and/or otherwise used.

The processor component 32 additionally determines MT properties of blood, for example, through a blood MR signal captured in the presence of off-resonance RF irradiation and a blood MR signal captured absent of off-resonance RF irradiation. The blood volume processor 32 quantifies parenchymal blood volume based on the MT properties of parenchyma, tissue and blood. The processing component 32 can also determine a blood volume effect in blood, and quantify an effect of blood volume change from a blood volume effect in parenchyma, tissue and blood. The resulting blood volume and/or the effect of blood volume change is displayed to the user on the user interface 34, stored in the storage component 30, and/or otherwise used.

In another instance, the blood volume processor 32 determines blood volume through magnetization transfer ratios (MTRs). The blood volume processor 32 computes blood volume through various algorithms. A suitable algorithm includes the following: $V_{par}(1-MTR_{par}/MTR_{tissue})$, where $V_{par}$ is a total parenchymal water volume, $MTR_{par}$ is the magnetization transfer ratio of parenchyma, and $MTR_{tissue}$ is the magnetization transfer ratio of tissue. The blood volume processor 32 computes $MTR_{par}$ as a ratio of a MR signal of parenchyma in the presence of off-resonance RF irradiation to a MR signal of parenchyma absent off-resonance RF irradiation. Similarly, the blood volume processor 32 computes $MTR_{tissue}$ as a ratio of a MR signal of tissue in the presence of off-resonance RF irradiation to a MR signal of tissue in the absence of off-resonance RF irradiation. Typically, the same off-resonance RF irradiation frequency, power, pulse length and number of pulses are used to determine both the $MTR_{par}$ and the $MTR_{tissue}$. The resulting blood volume is displayed to the user on the user interface 34, stored in storage, and/or otherwise used.

A magnetization transfer ratio of blood, $MTR_{blood}$, is also determined. The blood volume processor 32 computes $MTR_{blood}$ as a ratio of a MR signal of blood in the presence of off-resonance RF irradiation to a MR signal of blood absent off-resonance RF irradiation. The blood volume processor 32 computes blood volume based on the $MTR_{par}$, $MTR_{tissue}$, and $MTR_{blood}$. For example, the blood volume is quantified based at least in part on the following: $MTR_{par}=MTR_{tissue}-(MTR_{tissue}-MTR_{blood})(BV/V_{par})$. Typically, the off-resonance RF irradiation frequency, power, pulse length and number of pulses used to determine the $MTR_{par}$ and the $MTR_{tissue}$ are also used to determine the $MTR_{blood}$.

In yet another instance, the blood volume processor 32 determines the effect of blood volume changes in parenchyma based on data captured with and without physiological perturbations that affect blood volume. A scanning procedure can be performed without any perturbations to acquire data through the MT effect without a perturbation. A scanning procedure can also be performed with a perturbation to acquire data through the MT effect with a perturbation. The blood volume processor 32 computes the difference between the data with and without perturbations and quantifies the effect of blood volume changes through the change in MT effect. Suitable perturbations include $CO_2$ breathing, breath-hold, hyperventilation, brain activation, inhalation and/or ingestion of appropriate chemicals, and/or other perturbations that affect the blood volume. Alternatively, a spectroscopy apparatus or the like can be used to determine blood volume based on data captured with and without such perturbations.

The blood volume processor 32 also determines an effect of a blood volume change in parenchyma. For example, the blood volume processor 32 acquires a MR signal of parenchyma in a presence of off-resonance radio frequency (RF) irradiation and a MR signal of parenchyma in the absence of off-RF irradiation. The blood volume processor 32 then determines the MT of parenchyma based on the MR parenchyma signals.

The MR signals used by the processing component 32 to quantify the blood volume and/or measure the change in MT effect are obtained through imaging techniques such as spin echo, gradient echo, and/or stimulated echo, for example.

Figure 2:
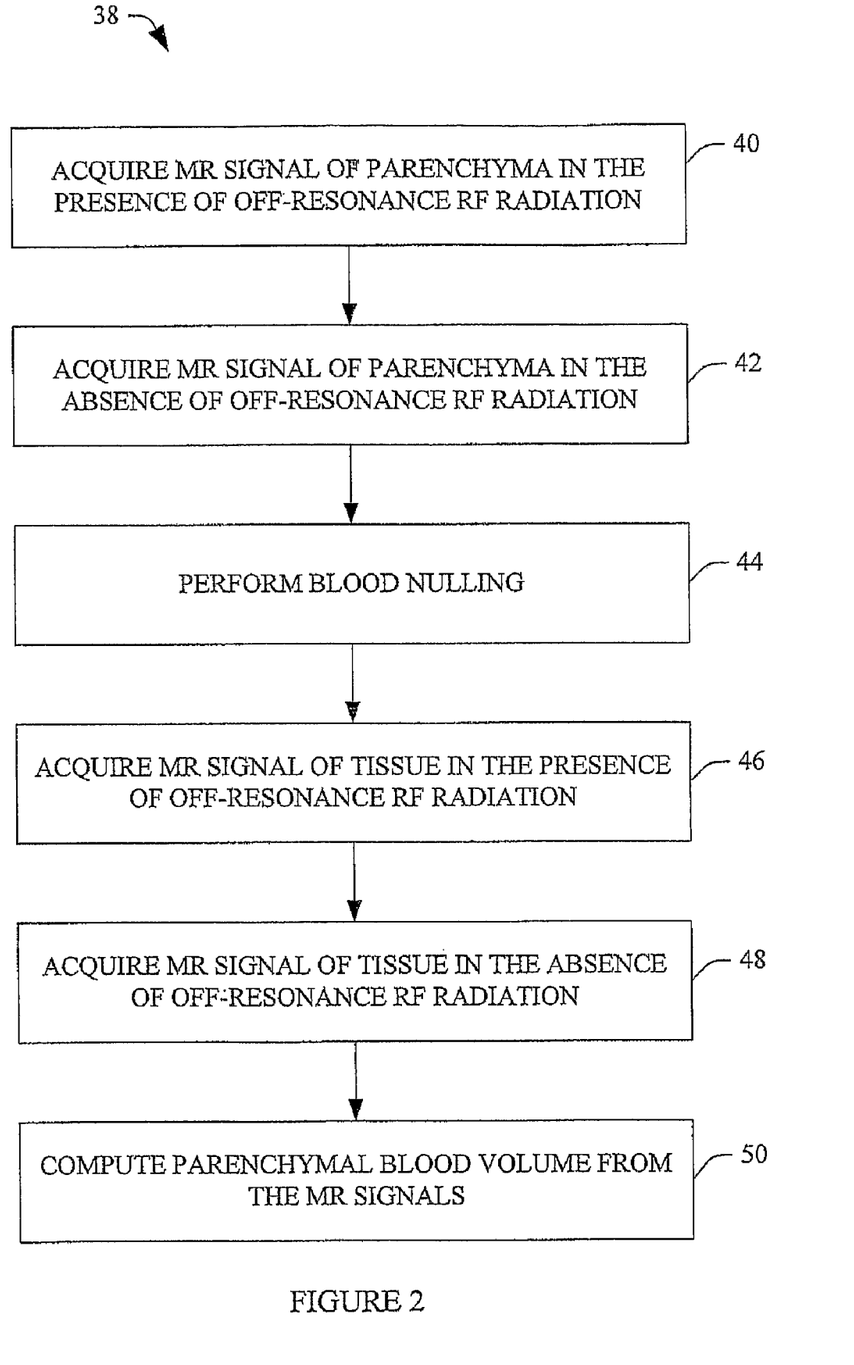
FIG. 2 illustrates a method for determining blood volume through a MT effect.

FIG. 2 illustrates a method 38 for determining blood volume (absolute and relative) through a MT effect. A suitable technique (e.g., MRI, spectroscopy . . . ) that renders a MT effect is used to determine MT properties of parenchyma. One such technique includes acquiring magnetic resonance (MR) signals for each voxel in the presence and absence of off-resonance RF irradiation. At reference numeral 40, a MR signal of parenchyma in the presence of off-resonance RF irradiation is acquired. At 42, a MR signal of parenchyma in the absence of off-resonance RF irradiation.

A suitable technique that renders an MT effect is used to determine properties of tissue (e.g., pure extravascular tissue). At reference numeral 44, a blood-nulling MR pulse sequence or another type of blood-nulling approach (e.g. using contrast agents) is performed. At 46, a MR signal of tissue in the presence of off-resonance RF irradiation is acquired. At 48, a MR signal of tissue the absence of off-resonance RF irradiation. The blood-nulling MR pulse sequence includes any MRI method or other method to remove an MRI signal from blood. Examples include, but are not limited to, at least one of the following: applying a 180 degree inversion RF pulse followed by a specific inversion recovery time that is able to null the blood magnetic resonance signal based on a correct T1 of blood water at a particular magnetic field strength; applying strong coherent flow-based or incoherent diffusion—based dephasing gradients during evolution of the magnetization before acquisition; exciting and de-phasing water protons in the blood before flowing into the slice of interest; and adding an agent (e.g. relaxation) to remove a water signal of blood.

At reference numeral 50, parenchymal blood volume is quantified based on the MT properties of parenchyma and the MT properties of tissue. For instance, the parenchymal blood volume can be computed from the difference between the MR signals of parenchyma and the MR signals of tissue. This blood volume indicates microvascular blood volume.

In an alternative embodiment, a MT effect in blood is also acquired. A suitable technique for determining the MT effect in blood includes acquiring a MR signal of blood in the presence of off-resonance RF irradiation and acquiring a MR signal of blood in the absence of off-resonance RF irradiation. The MR signals are one of isolated blood signals in vivo and blood signals from a blood phantom maintained under physiological conditions. The parenchymal blood volume is then quantified based on the MT properties of parenchyma, the MT properties of tissue, and the MT properties of blood.

Figure 3:
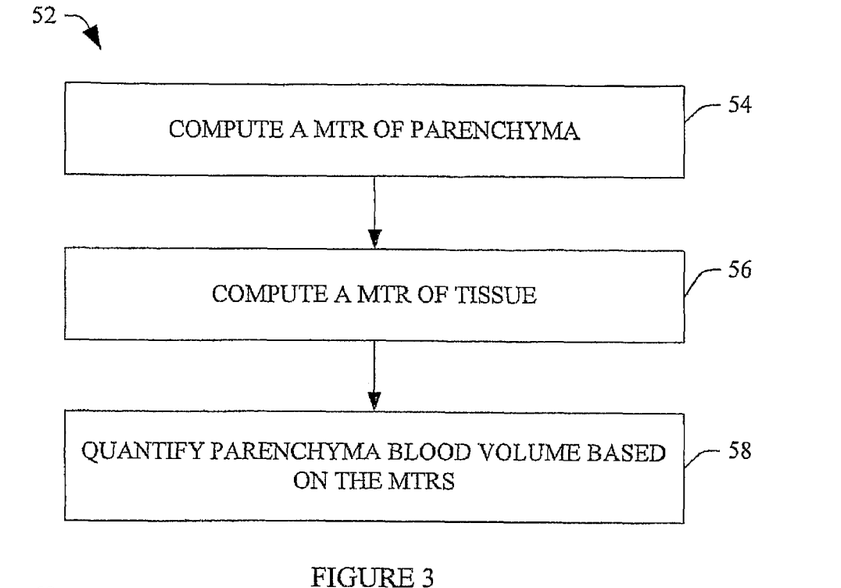
FIG. 3 illustrates a method for determining blood volume through magnetization transfer ratios (MTRs).

FIG. 3 illustrates a method 52 for determining blood volume (absolute and relative) through magnetization transfer ratios (MTRs). At 54, a magnetization transfer ratio of parenchyma, $MTR_{par}$, is determined. A suitable technique for determining $MTR_{par}$ includes: acquiring a MR signal of parenchyma in the presence of off-resonance RF irradiation; acquiring a MR signal of parenchyma absent off-resonance RF irradiation; and calculating the MTR of parenchyma as a ratio of the MR signal of parenchyma in the presence of off-resonance RF irradiation to the MR signal of parenchyma absent off-resonance RF irradiation.

At reference numeral 56, a magnetization transfer ratio of tissue $MTR_{tissue}$ is determined. A suitable technique for determining $MTR_{tissue}$ includes: performing a blood-nulling MR pulse sequence or any other approach that nulls the MR blood signal; acquiring a MR signal of tissue in the presence of off-resonance RF irradiation; acquiring a MR signal of tissue in the absence of off-resonance RF irradiation; and calculating the MTR of tissue as a ratio of the MR signal of tissue in the presence of off-resonance RF irradiation to the MR signal of tissue absent off-resonance RF irradiation. Typically, the same off-resonance RF irradiation frequency of the same power, length and number of pulses is used to determine both the $MTR_{par}$ and the $MTR_{tissue}$. The blood-nulling MR pulse sequence includes any MRI method or other method to remove the MRI signal from the blood as describe supra.

At reference numeral 58, parenchymal blood volume is quantified based on a relationship between $MTR_{par}$ and $MTR_{tissue}$. For example, the blood volume can be quantified based at least in part on the following: $BV=V_{par}(1-MTR_{par}/MTR_{tissue})$, where $V_{par}$ is the total parenchymal water volume. Blood volume can alternatively be obtained by varying the MTR of tissue and/or parenchyma as a function of at least one of radio frequency power, offset, angle, phase and length, and/or the number of pulses.

A magnetization transfer ratio of blood, $MTR_{blood}$, can also be obtained. A suitable technique for determining $MTR_{blood}$ includes acquiring a MR signal of blood in the presence of off-resonance RF irradiation; acquiring a MR signal of blood in the absence of off-resonance RF irradiation; and using the MR signal of blood in the presence of off-resonance RF irradiation and the MR signal of blood in the absence of off-resonance RF irradiation to calculate the MTR of blood. The parenchymal blood volume is quantified based on $MTR_{par}$, $MTR_{tissue}$, and $MTR_{blood}$. For example, the blood volume can be quantified based at least in part on the following: $MTR_{par}=MTR_{tissue}-(MTR_{tissue}-MTR_{blood})(BV/V_{par})$.

Figure 4:
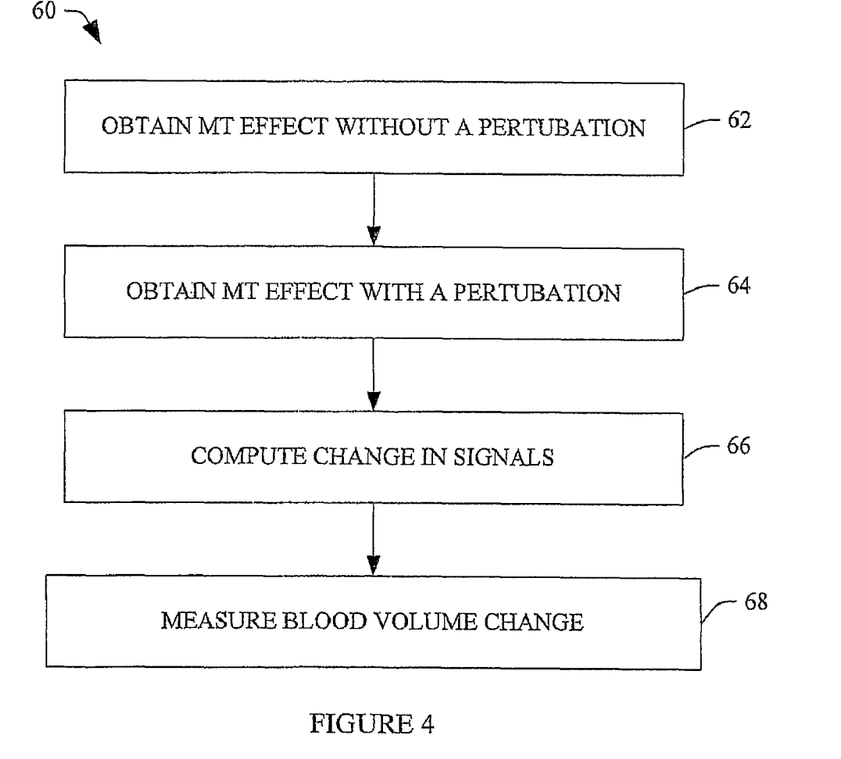
FIG. 4 illustrates a method for determining the blood volume effect through physiological perturbations.

FIG. 4 illustrates a method 60 for determining a blood volume change through introducing or suppressing physiological perturbations that affect blood volume. Suitable perturbations include $CO_2$ breathing, breathhold, hyperventilation, brain activation, inhalation and/or ingestion of appropriate chemicals, and/or other perturbations that affect the MT effect. At reference numeral 62, a signal associated with the MT effect without a perturbation is obtained. At 64, a signal associated with the MT effect with a perturbation is obtained. At 66, a change between the signals that is indicative of a change in the MT effect without the perturbation and with the perturbation is computed. A suitable technique for determining the effect of blood volume changes in parenchyma includes acquiring a MR signal of parenchyma in a presence of off-resonance radio frequency (RF) irradiation, acquiring a MR signal of parenchyma in the absence of off-RF irradiation, and determining the MT of parenchyma based on the MR parenchyma signals. At reference numeral 68, the change is used to quantify the effect of blood volume changes in parenchyma. A MRI system, a spectroscopy apparatus, or the like is used perform these acts and determine the effect of blood volume changes in parenchyma.

The following describes an exemplary technique to derive a model that computes blood volume as a function of MT signal attenuation in tissue and MT signal attenuation in parenchyma. It is to be understood that the following is provided for explanatory purposes and is not limitative. One skilled in the art will recognize that other techniques can be used to derive one or more other models that compute blood volume as a function of MT signal attenuation in tissue, parenchyma, blood, etc.

Parenchyma is the functional parts (e.g., the essential and distinctive tissue) of an organ in the body. By way of example, the nephrons of the kidney and the alveoli of the lungs are parenchyma. The parenchyma is composed of microvessels and extravascular tissue. The microvasculature includes arterioles, capillaries, and venules, all of which determine the total blood volume. For instance, the total blood volume can be computed through $BV=\Sigma_i BV_i$ where blood volume is summed over arteriolar, capillary, and venular blood (e.g., i=arteriolar, capillary, and venular blood). The extravascular tissue consists of many components, including tissue water and semi-solid macromolecules. The macromolecules have a spectral width of tens of kHz.

By saturating the broad macromolecular phase by an off-resonance radio frequency (RF) field, a magnetic resonance (MR) signal of the tissue water reduces due to a transfer of saturation from a semi-solid pool of protons to the water protons. This transfer is referred to as a magnetization transfer (MT) effect and is commonly described by a magnetization transfer ratio, $MTR=1-S_{sat}/S_{unsat}$, where $S_{sat}$ is a saturated (with RF irradiation) imaging signal intensity and $S_{unsat}$ is an unsaturated (without RF irradiation) imaging signal intensity. Because blood is perturbed less with off-resonance irradiation, the signal contribution of microvascular blood water to the total parenchyma MR signal will increase, depending on the off-resonance irradiation power, offset, phase, length, angle, number of pulses, and other MR and tissue parameters. Blood volume can be measured by varying at least one of these parameters.

With MRI, measured signal intensities of water reflect the effect of physiological changes in multi-component voxels. Each voxel component (e.g., tissue, blood . . . ) has individual tissue relaxation and MT parameters, and each component's relative contribution depends on the size and location of the voxel and the MRI acquisition parameters. For homogeneously perfused tissue, such as parenchyma, the normalized imaging signal intensity ($S_{par}$), as a function of echo time (TE), is a multi-exponential decaying process expressed by Equation 1:

$$S_{par} = x_{tissue}S_{tissue} + \sum_i x_{blood,i}S_{blood,i}, \qquad 1$$
$$= x_{tissue}\eta_{tissue}e^{-R_{2,tissue}TE} + \sum_i x_{blood,i}\eta_{blood,i}e^{-R_{2,blood,i}TE},$$

where $x_{tissue}$ is a water fraction of tissue, $S_{tissue}$ is an imaging signal intensity of tissue, $x_{blood}$ is a water fraction of blood, $S_{blood}$ is an imaging signal intensity of blood, $\eta_{tissue}$ is a multiplication factor or coefficient, $R_2$ is a transverse relaxation rate, TE is an echo time, and i is a variable that indicates the particular blood compartment. The summation for the blood compartments sums over arteriolar, capillary, and venular blood (e.g., i=arteriole, capillary and venule). The blood water fractions reflect a ratio of blood volume to parenchymal volume, $BV_i/V_{par}$. The total water content during physiological perturbations is $x_{tissue}+\Sigma_i x_{blood,i}$, which is equal to one.

With substantially complete relaxation at the end of each scan (where TR is much greater than $T_1$), a 90-180 degree SE acquisition sequence without MT, or unsaturated, ($S_{par,unsat}$) is expressed by Equation 2:

$$S_{par,unsat} = x_{tissue}e^{-R_{2,tissue}TE} + \sum_i x_{blood,i}e^{-R_{2,blood,i}TE}, \qquad 2$$

and a 90-180 degree SE acquisition sequence with MT, or saturated, ($S_{par,sat}$) is expressed by Equation 3:

$$S_{par,sat} = x_{tissue}(1 - MTR_{tissue})e^{-R_{2,tissue}TE} + \qquad 3$$
$$\sum_i x_{blood,i}(1 - MTR_{blood,i})e^{-R_{2,blood,i}TE},$$

where $(1-MTR_{tissue})$ is a conventional MT signal attenuation in tissue and $(1-MTR_{blood})$ is a conventional MT signal attenuation in blood. With negligible MT effect on the blood (e.g., when RF irradiation is far from the water resonance), Equation 3 is expressed by Equation 4:

$$S_{par,sat} = x_{tissue}(1 - MTR_{tissue})e^{-R_{2,tissue}TE} + \sum_i x_{blood,i} e^{-R_{2,blood,i}TE}$$

$$= (1 - MTR_{tissue})\left(x_{tissue}e^{-R_{2,tissue}TE} + \sum_i x_{blood,i} e^{-R_{2,blood,i}TE}\right) + MTR_{tissue}\sum_i x_{blood,i} e^{-R_{2,blood,i}TE}.$$ (4)

The z-spectrum of parenchyma (signal intensities normalized to the corresponding unsaturated case) is expressed by Equation 5:

$$\frac{S_{par,sat}}{S_{par,unsat}} = (1 - MTR_{par})$$

$$= (1 - MTR_{tissue}) + MTR_{tissue}\frac{\sum_i x_{blood,i} e^{-R_{2,blood,i}TE}}{x_{tissue}e^{-R_{2,tissue}TE} + \sum_i x_{blood,i} e^{-R_{2,blood,i}TE}},$$ (5)

where $(1-MTR_{par})$ is a MT signal attenuation in parenchyma. The second term of Equation 5 describes apparent reduction in the MT effect (e.g., decreased $MTR_{par}$) caused by an increased blood signal contribution.

Equation 5 indicates blood volume contribution to the signal increases when applying radio frequency. One approach to achieve absolute quantification is to assume negligible MT effects in blood or account for limited MT effect in blood by measuring blood MT through in vitro techniques, for example, using a physiological blood phantom and other blood relaxation measurements. When neglecting the blood MT, using a long repetition time (TR) and a very short echo time (TE), employing a parenchymal selection approach (e.g., by using sufficiently high spatial resolution or by using a physiological paradigm and a parenchymal functional MRI approach), Equation 5 simplifies to Equation 6:

$$(1-MTR_{par})=(1-MTR_{tissue})+MTR_{tissue}(BV/V_{par}),$$ (6)

where BV is blood volume and $V_{par}$ is the total parenchymal water volume. The parameters and/or variables of Equation 6 can be re-arranged to render Equation 7:

$$MTR_{par}=MTR_{tissue}(1-BV/V_{par}).$$ (7)

or Equation 8:

$$BV=V_{par}(1-MTR_{par}/MTR_{tissue}).$$ (8)

Both Equation 7 and Equation 8 show that blood volume can be quantified through $MTR_{par}$ and $MTR_{tissue}$ measurements. $MTR_{par}$ is measured by conventional MT techniques, and $MTR_{tissue}$ is measured by blood-nulling techniques such as the VASO approach or other techniques such as the use of gradients for flow and/or diffusion nulling. Other MRI and/or chemical/medical approaches to null the MRI signal of blood water could alternatively be used. At longer echo times, the transverse relaxation rates of tissue and parenchyma are measured using approaches with and without blood nulling.

The interaction between MT and BOLD provides a novel MRI approach to measure cerebral blood volume (CBV) in vivo. For instance, when TE is relatively short, Equations 7 and 8 are respectively expressed by Equations 9 and 10:

$$MTR_{par}=MTR_{tissue}(1-CBV/V_{par}), \text{ and}$$ (9)

$$CBV=V_{par}(1-MTR_{par}/MTR_{tissue}),$$ (10)

where CBV is cerebral blood volume. This can also be done in tissues other than brain (e.g., heart, etc., where it would be myocardial BV).

The following further quantifies the effect of physiological adjustments in a BOLD-type approach. The relative signal intensity is defined with respect to a normal physiological state, and, assuming unchanged tissue MTR during blood-based physiological changes, the ratio of the signal intensity of parenchyma can be expressed by Equation 11:

$$\frac{S_{par,sat}}{S_{par,sat}^{norm}} = (1 - MTR_{tissue})\frac{x_{tissue}e^{-R_{2,tissue}TE} + \sum x_{blood,i} e^{-R_{2,blood,i}TE}}{x_{tissue}^{norm}(1 - MTR_{tissue})e^{-R_{2,tissue}^{norm}TE} + \sum x_{blood,i}^{norm} e^{-R_{2,blood,i}^{norm}TE}} + MTR_{tissue}\frac{\sum x_{blood,i} e^{-R_{2,blood,i}TE}}{x_{tissue}^{norm}(1 - MTR_{tissue})e^{-R_{2,tissue}^{norm}TE} + \sum x_{blood,i}^{norm} e^{-R_{2,blood,i}^{norm}TE}}.$$ (11)

When applied to quantify the BOLD effect, the first term in Equation 11 is very similar (slightly smaller) to the conventional SE BOLD effects, and the second part describes the BOLD enhancement due to RF saturation. In the absence of RF irradiation, $MTR_{tissue}=0$, and only the first term remains.

As shown in Equation 12:

$$\frac{\Delta S_{par,sat}}{S_{par,sat}^{norm}} = \frac{(1 - MTR_{tissue})(x_{tissue}e^{-R_{2,tissue}TE} - x_{tissue}^{norm}e^{-R_{2,tissue}^{norm}TE}) + \sum(x_{blood,i}e^{-R_{2,blood,i}TE} - x_{blood,i}^{norm}e^{-R_{2,blood,i}^{norm}TE})}{x_{tissue}^{norm}(1 - MTR_{tissue})e^{-R_{2,tissue}^{norm}TE} + \sum x_{blood,i}^{norm} e^{-R_{2,blood,i}^{norm}TE}},$$ (12)

$S_{par,sat}/S_{par,sat}^{norm}$ (MT BOLD plus traditional SE BOLD) is more sensitive to the physiological changes (larger effect) than $S_{par,sat}/S_{par,unsat}$ (MT BOLD only). The BOLD signal changes after a period of saturation. The tissue contribution after saturation (the first term) is always smaller than, or approximately equal to the standard tissue BOLD effect in parenchyma, while the blood BOLD contribution is always increased (about doubled if $MTR_{tissue}$ is a bit more than 50%). Equation 12 indicates that mixing of MT and BOLD experiments can provide new information regarding blood volume as well as the intravascular contribution to the BOLD effect.

Figure 5:
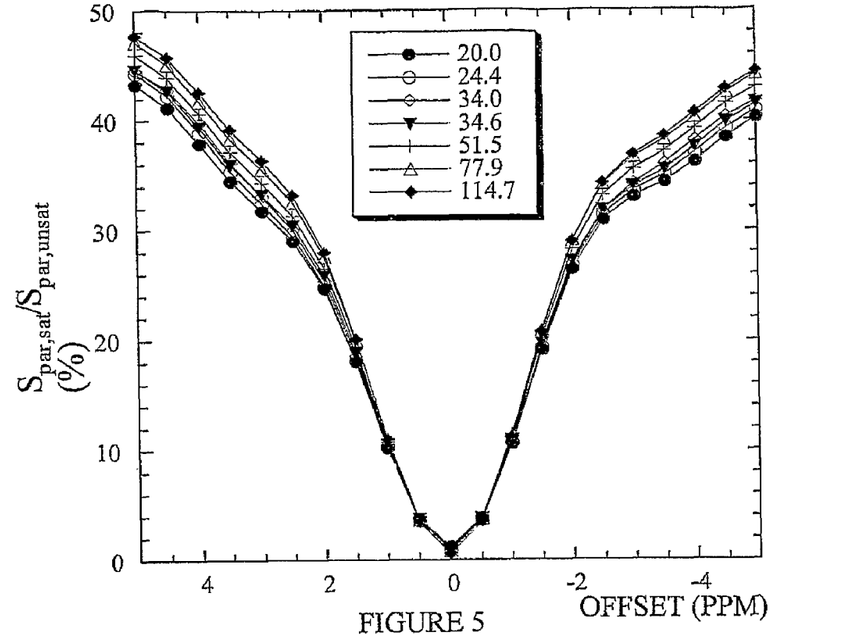
FIG. 5 illustrates z-spectra for a narrow saturation offset frequency range at different arterial $PCO_2$ levels.
Figure 6:
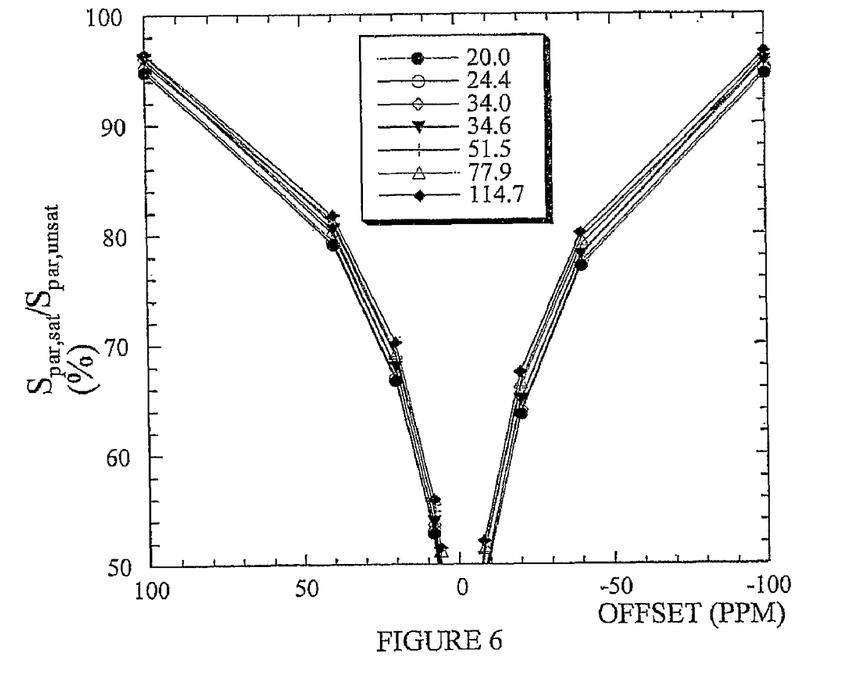
FIG. 6 illustrates z-spectra for a wide saturation offset frequency range at different arterial $PCO_2$ levels.
Figure 7:
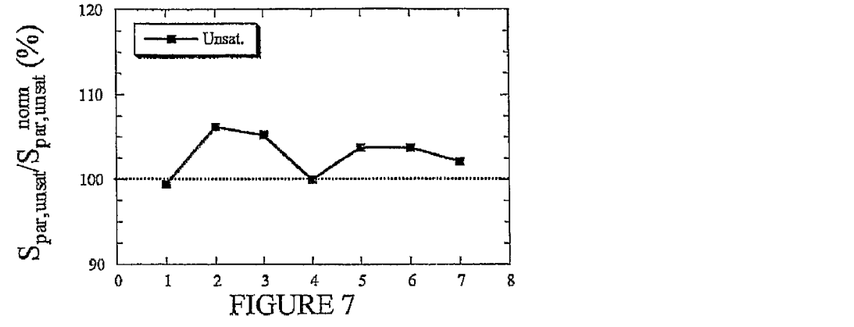
FIG. 7 illustrates a BOLD-type response of signal intensities to arterial $PCO_2$ changes in the absence of RF irradiation.
Figure 8:
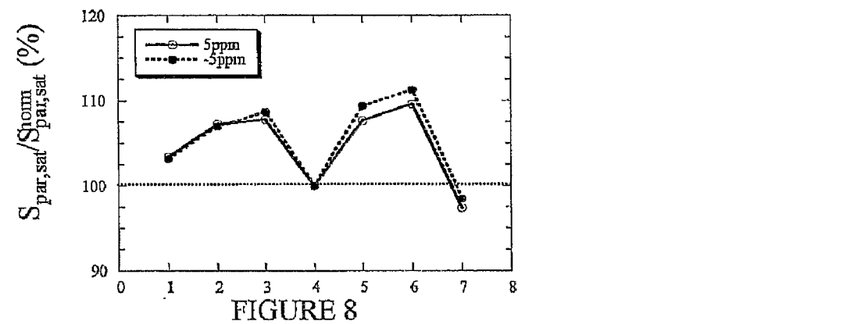
FIGS. 8-10 illustrate a BOLD-type response of signal intensities to arterial $PCO_2$ changes in the presence of RF irradiation.
Figure 9:
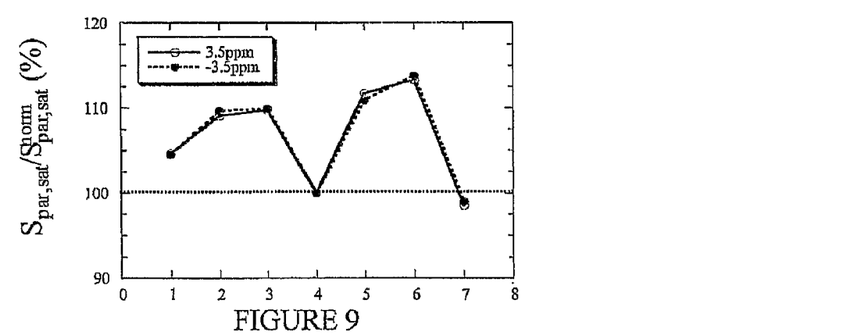
Figure 10:
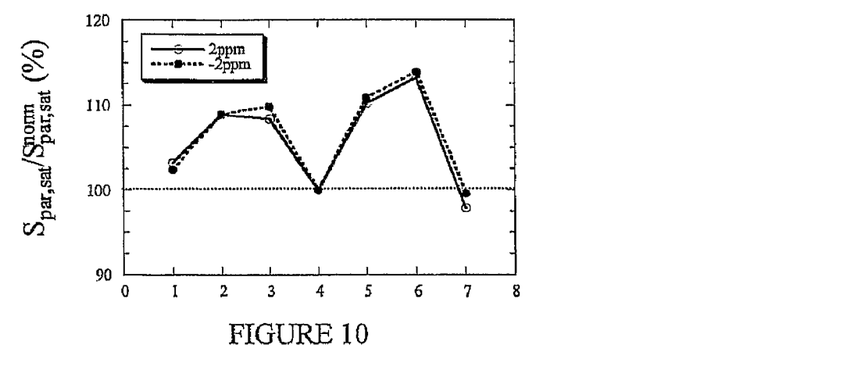
Figure 11:
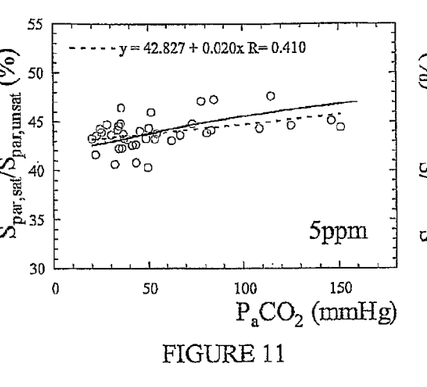
FIGS. 11-16 illustrate MT-based signal intensities normalized to corresponding unsaturated cases as a function of arterial $PCO_2$ value.
Figure 12:
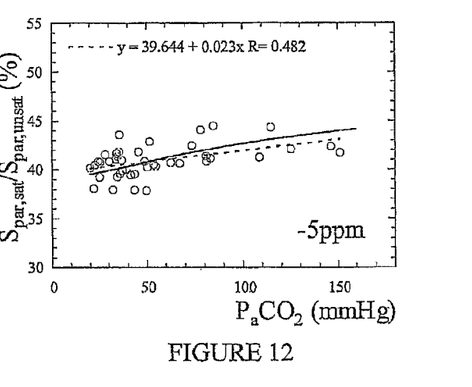
Figure 13:
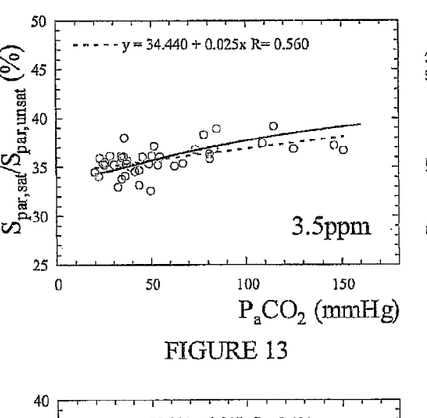
Figure 14:
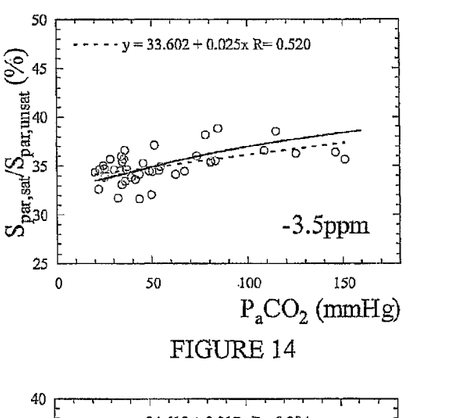
Figure 15:
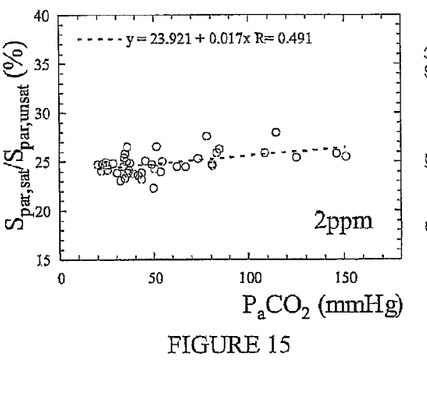
Figure 16:
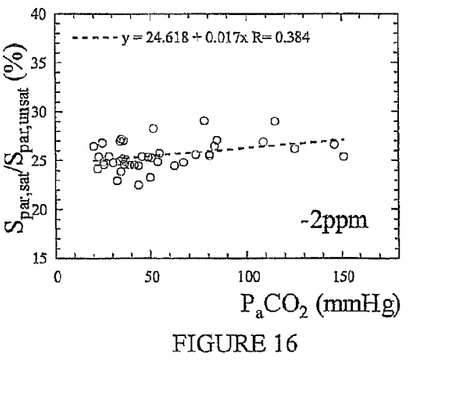
Figure 17:
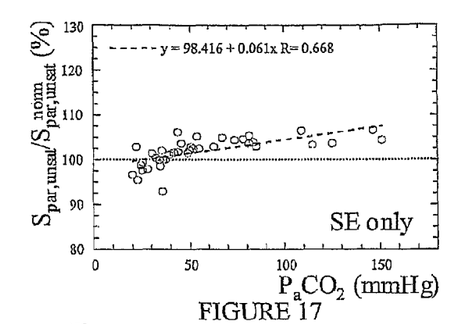
FIGS. 17-23 illustrate an arterial $PCO_2$ dependence at several saturation offsets for the BOLD-type signal intensities, normalized with respect to normocapnia.
Figure 18:
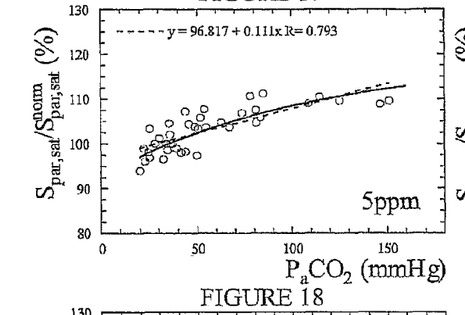
Figure 19:
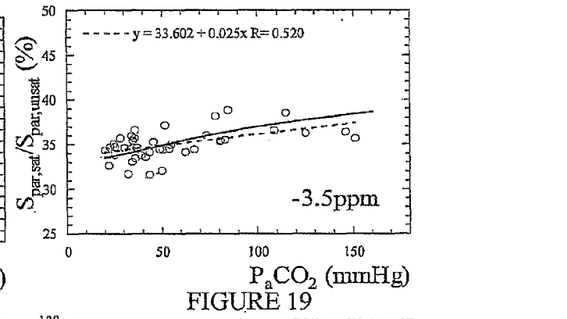
Figure 20:
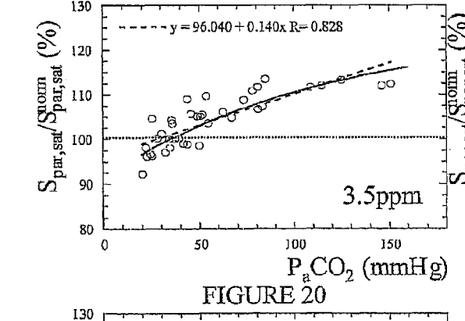
Figure 21:
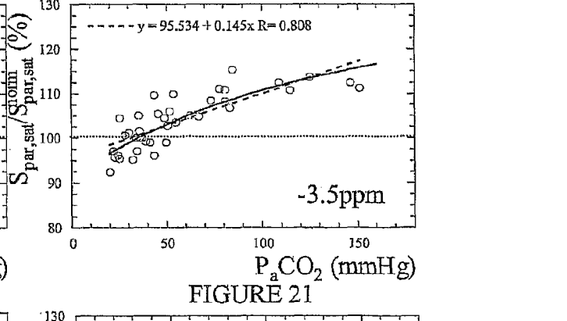
Figure 22:
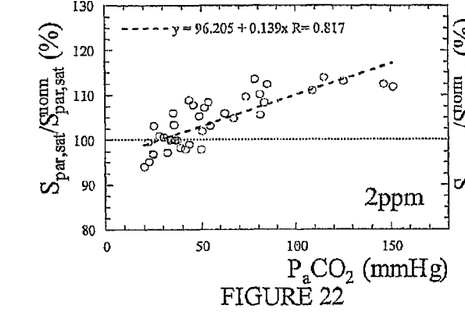
Figure 23:
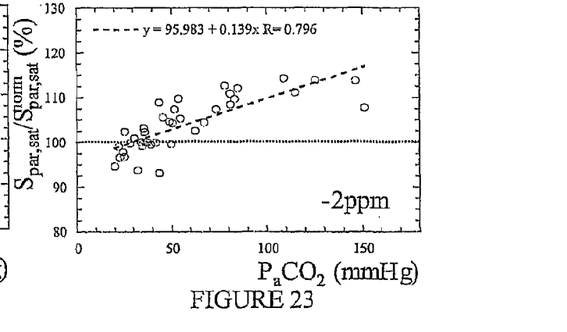
Figure 24:
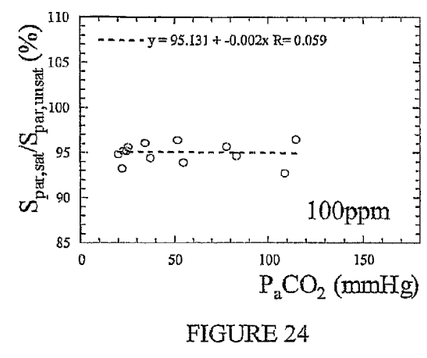
FIGS. 24-27 illustrate results for MT-based signal intensities as a function of arterial $PCO_2$ level at four large offsets.
Figure 25:
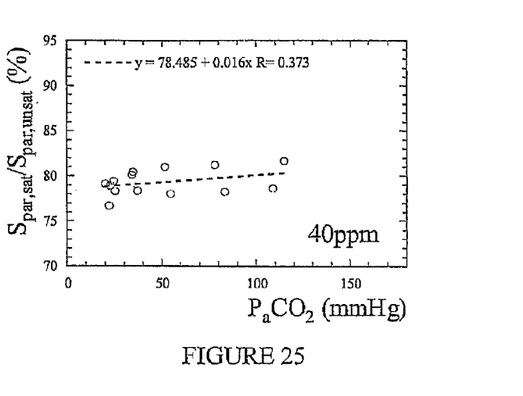
Figure 26:
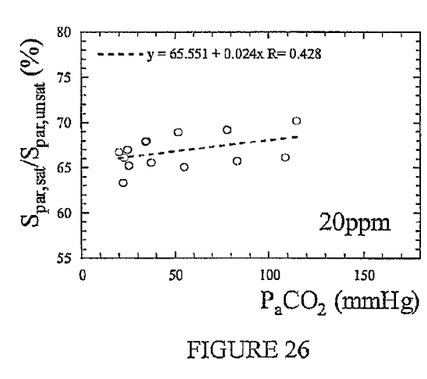
Figure 27:
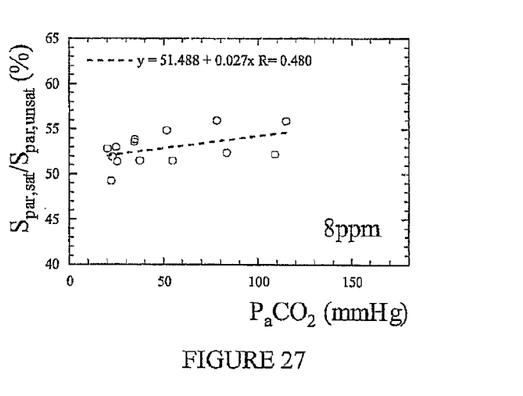
Figure 28:
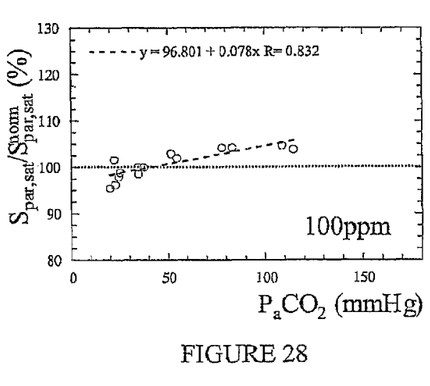
FIGS. 28-31 illustrate results for BOLD-based signal intensities as a function of arterial $PCO_2$ value at four large offsets.
Figure 29:
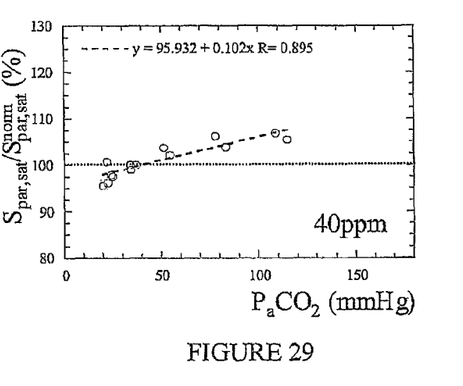
Figure 30:
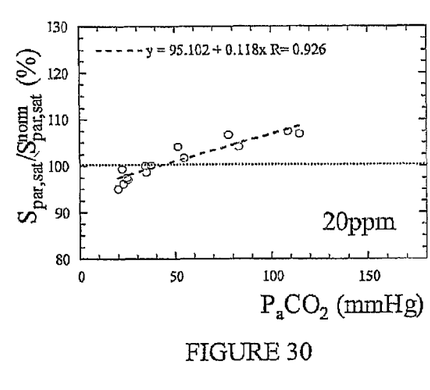
Figure 31:
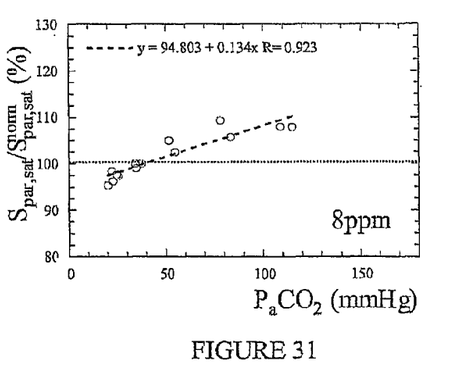

FIGS. 5-6 illustrate experimental results demonstrating the principles described herein. FIGS. 5 and 6 show acquired z-spectra ($S_{par,sat}/S_{par,unsat}$) in the brain as a function of a narrow (FIG. 5) and a wide (FIG. 6) saturation offset frequency at seven arterial $PCO_2$ levels for a typical rat. The data was generated with a low RF power of about 2 μT. The signal intensities are normalized to the corresponding unsaturated cases. The measured signal intensities of parenchyma increase and MTR decreases with increased arterial $PCO_2$. Approximately 35% and 45% signal remains at offsets of 3.5 and 5 ppm, respectively. The z-spectra indicate $PCO_2$-dependence and are slightly asymmetric with respect to water resonance, with a center frequency in the upfield (lower frequency) range.

FIGS. 7-10 show the BOLD-type response of the signal intensities to arterial $PCO_2$ changes in the absence (FIG. 7) and presence (FIGS. 8-10) of RF irradiation for a rat. The arterial $PCO_2$ levels were 25.2, 43.6, 53.7, 34.3, 80.7, 125.0, and 49.7 mmHg, respectively. The signal intensities are normalized to the fourth physiological state ($P_aCO_2$=34.3 mmHg, $pH_a$=7.434). When using a BOLD-type approach and normalizing the signal intensities for all the offsets and the unsaturated case to one selected normocapnia level ($S_{par,sat}/S_{par,sat}^{norm}$), the signal intensities have a similar range of magnitudes. At a 100 mmHg change in $PCO_2$, there is a change of about 7% in the unsaturated, non-irradiated signal intensities (standard SE BOLD effect), but an increased magnitude up to approximately 15% for the signal intensities under off-resonance RF irradiation (combined MT BOLD and standard SE BOLD effect). This is due to the enhance contribution of the blood signal.

FIGS. 11-16 shows the MT-based signal intensities normalized to corresponding unsaturated cases as a function of arterial $PCO_2$ value for six rats, and FIGS. 17-23 depict an arterial $PCO_2$ dependence at several saturation offsets for the BOLD-type signal intensities ($S_{par,sat}/S_{par,sat}^{norm}$), normalized with respect to normocapnia. The solid lines in all the figures are the results fitted with the theory. Using the $S_{par,sat}/S_{par,unsat}$–$P_aCO_2$ data and $CBV_{norm}$=4.6 ml blood/100 g brain, the fitted $(1-MTR_{tissue})$ is 0.418, 0.334, 0.326, and 0.387 at the offsets of 5, 3.5, -3.5, and -5 ppm, respectively. Based on these fitted $(1-MTR_{tissue})$ values, $CBV_{norm}$=3.9 ml blood/100 g brain is then obtained from the $S_{par,sat}/S_{par,sat}^{norm}$–$P_aCO_2$ data. Negligible blood signal intensity attenuation upon saturation is assumed.

The dashed lines correspond to approximate linear fitting. Table 1 lists the fitted slope values for these offsets, showing a very similar $P_aCO_2$ dependence for the positive and negative offset sides. For an arterial $PCO_2$ increase of 100 mmHg, $S_{par,sat}/S_{par,unsat}$ increases by about 2-3%, while $S_{par,sat}/S_{par,sat}^{norm}$ increases by about 11-15%. The slope values for MT-modulated BOLD effect are about two times larger than those for the unsaturated signal intensities, corresponding to the common SE BOLD effect.

Even though relatively weak RF irradiation is used, the effects of direct saturation are substantial around the water peak at 4.7 ppm, which gradually reduces at increased offsets. Several additional large offsets were acquired for two of six animals to illustrate the effects at wider offsets. FIGS. 24-31 show the results for the BOLD-based signal intensities as a function of arterial $PCO_2$ level. In particular, FIGS. 24-27 correspond to unsaturated cases, and FIGS. 28-31 correspond to one normocapnic state as a function of arterial $PCO_2$ value at four large offsets for two rats. The reference states are in Table 1.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A magnetic resonance (MR) method for quantifying the blood volume in parenchyma via a magnetization transfer (MT) effect, comprising:
    determining a MT effect in parenchyma by operations including acquiring a MR signal of parenchyma in a presence of off-resonance radio frequency (RF) irradiation, acquiring a MR signal of parenchyma in the absence of off-resonance RF irradiation, and determining the MT of parenchyma based on the parenchymal MR signals;
    determining a MT effect in tissue;
    determining a MT effect in blood; and
    quantifying the parenchymal blood volume based on the MT effect of parenchyma, the MT effect of tissue, and the MT effect of blood.

2. The method of claim 1, wherein determining the MT of tissue includes:
    performing a blood-nulling MR pulse sequence;
    acquiring a MR signal of tissue in the presence of off-resonance RF irradiation;
    acquiring a MR signal of tissue in the absence of off-resonance RF irradiation; and
    determining the MT of tissue based on the MR tissue signals.

3. The method of claim 2, wherein performing a blood-nulling MR pulse sequence includes at least one of the following:

TABLE 1

Slope values of linear fitting to the percentage signal intensities (normalized to unsaturated cases and to normocapnic state for each animal) as a function of arterial $PCO_2$ for six rats. The unit is %/mmHg.

|  | 5 ppm | 3.5 ppm | 2 ppm | -2 ppm | -3.5 ppm | -5 ppm | Unsat. |
|---|---|---|---|---|---|---|---|
| $S_{par,sat}/S_{par,unsat}$ | 0.020 | 0.025 | 0.017 | 0.017 | 0.025 | 0.023 | — |
| $S_{par,sat}/S_{par,sat}^{norm}$ | 0.111 | 0.140 | 0.139 | 0.139 | 0.145 | 0.124 | 0.061 |

The reference states for each rat are in Table 2. There were 3 or 4 normocapnic states for each rat. The reference state is selected according to $P_aCO_2$ (~35 mmHg) and $pH_a$ (~7.4). The first state is chosen when two or more states fulfill the criteria.

TABLE 2

Physiological parameters of the selected reference states for six rats.

|  | 1 | 2 | 3 | 4 | 5 | 6 | Average |
|---|---|---|---|---|---|---|---|
| $P_aCO_2$ (mmHg) | 36.0 | 36.7 | 33.7 | 34.3 | 37.2 | 34.0 | 35.0 ± 1.3 |
| $pH_a$ | 7.379 | 7.426 | 7.448 | 7.434 | 7.392 | 7.351 | 7.422 ± 0.026 | applying a 180 degree inversion radio frequency pulse followed by an inversion recovery time that nulls a blood MR signal based on a correct $T_1$ of blood water at a particular magnetic field strength;

applying one of a strong coherent flow-based and an incoherent diffusion-based de-phasing gradient during evolution of the magnetization before acquisition;

exciting and de-phasing water protons in the blood before flowing into a slice of interest; and nulling a MR signal of blood.

4. The method of claim 3, wherein nulling the MR signal of blood includes adding a relaxation agent to remove a water signal of blood.

5. The method of claim 1, wherein determining the MT of blood includes:

acquiring a MR signal of blood in a presence of off-resonance RF irradiation;

acquiring a MR signal of blood in the absence of off-resonance RF irradiation; and determining the MT of blood based on the blood MR signals.

6. The method of claim 5, wherein the blood MR signals are one of the following:

isolated blood signals in vivo, and blood signals from a blood phantom maintained under physiological conditions.

7. The method of claim 1 further including:

determining the MT effect without a perturbation;

determining the MT effect with a perturbation; and computing the effect of a blood volume change using the difference between the MT effect without the perturbation and the MT effect with the perturbation.

8. The method of claim 7, further including introducing the perturbation through at least one of the following: $CO_2$ breathing, breathhold, hyperventilation, brain activation, inhale chemicals, and ingested chemicals.

9. A magnetic resonance (MR) method for quantifying the blood volume in parenchyma via magnetization transfer ratio (MTR) comprising:

determining a MTR in parenchyma by operations including acquiring a MR signal of parenchyma in a presence of off-resonance radio frequency (RF) irradiation, acquiring a MR signal of parenchyma in the absence of off-resonance RF irradiation, and determining the MTR of parenchyma based on the parenchymal MR signals;

determining a MTR of tissue; and quantifying the parenchymal blood volume based on the MTR of parenchyma and the MTR of tissue.

10. The method of claim 9, wherein quantifying the parenchymal blood volume based on the MTR of parenchyma and the MTR of tissue includes computing blood volume through the following:

$$MTR_{par}=MTR_{tissue}(1-BV/V_{par}),$$

where $MTR_{par}$ is the magnetization transfer ratio of parenchyma, $MTR_{tissue}$ is the magnetization transfer ratio of tissue, BV is the blood volume, and $V_{par}$ is a total parenchymal water volume.

11. The method of claim 9, wherein quantifying the parenchymal blood volume includes determining a difference between the MTR of parenchyma and the MTR of tissue.

12. The method of claim 9, wherein determining the MTR of tissue includes:

performing a blood-nulling MR pulse sequence;

acquiring a MR signal of tissue in the presence of off-resonance RF irradiation;

acquiring a MR signal of tissue in the absence of off-resonance RF irradiation; and using the MR signal of tissue in the presence of off-resonance RF irradiation and the MR signal of tissue in the absence of off-resonance RF irradiation to calculate the MTR of tissue.

13. The method of claim 12, wherein performing a blood-nulling MR pulse sequence includes at least one of the following:

applying a 180 degree inversion radio frequency pulse followed by an inversion recovery time that nulls a blood MR signal based on a correct $T_1$ of blood water at a particular magnetic field strength;

applying one of a strong coherent flow-based and an incoherent diffusion-based de-phasing gradient during evolution of the magnetization before acquisition;

exciting and de-phasing water protons in the blood before flowing into a slice of interest; and nulling a MR signal of blood.

14. The method of claim 13, wherein nulling the MR signal of blood includes adding a relaxation agent to remove a water signal of blood.

15. The method of claim 9, wherein the MTR of parenchyma and the MTR of tissue are determined as a function of an equivalent off-resonance radio frequency irradiation frequency.

16. The method of claim 9, wherein determining the parenchymal blood volume includes varying one or more of the MTR of parenchyma and the MTR of tissue as a function of at least one of radio frequency power, offset, angle, length, phase, and pulse number.

17. A magnetic resonance (MR) method for quantifying the blood volume in parenchyma via magnetization transfer ratio (MTR) comprising:

determining the MTR of blood by operations including acquiring a MR signal of blood in the presence of off-resonance radio frequency (RF) irradiation, acquiring a MR signal of blood in the absence of off-resonance RF irradiation, and determining the MTR of blood based on the blood MR signals; and determining a MTR of parenchyma, determining a MTR of tissue; and quantifying the parenchymal blood volume based on the MTR of parenchyma, the MTR of tissue, and the MTR of blood.

18. The method of claim 17, wherein quantifying the parenchymal blood volume based on the MTR of parenchyma, the MTR of tissue, and the MTR of blood includes computing blood volume through the following:

$$MTR_{par}=MTR_{tissue}-(MTR_{tissue}-MTR_{blood})(BV/V_{par}),$$

where $MTR_{par}$ is the magnetization transfer ratio of parenchyma, $MTR_{tissue}$ is the magnetization transfer ratio of tissue, $MTR_{blood}$ is the magnetization transfer ratio of blood, BV is the blood volume, and $V_{par}$ is a total parenchymal water volume.

19. The method of claim 17, wherein the MTR of parenchyma, the MTR of tissue, and the MTR of blood are determined as a function of an equivalent off-resonance radio frequency irradiation frequency.

20. The method of claim 17, wherein determining the parenchymal blood volume includes varying one or more of the MTR of parenchyma, the MTR of tissue, and the MTR of blood as a function of at least one of radio frequency power, offset, angle, length, phase, and number of pulses.

21. A MRI system, comprising:
a magnet that generates a magnetic field ($B_0$) in an examination region;
a gradient coil that superimposes magnetic field gradients on $B_0$;
a RF coil that introduces RF pulses to invoke a magnetization transfer (MT) effect during scanning;
a scan controller which controls the gradient and RF coils to perform a magnetization MT imaging sequence; and
a processing component that receives MR signals and quantifies blood volume based on the MR signals, the processing component being programmed to:
determine a MT effect in parenchyma;
determine a MT effect in tissue;
determine a MT effect in blood; and
quantify the parenchymal blood volume based on the MT effect of parenchyma, the MT effect of tissue, and the MT effect of blood.

22. The MRI system of claim 21, wherein the processing component is programmed to:
determine a magnetization transfer ratio (MTR) in parenchyma;
determine a MTR of tissue; and
quantify the parenchymal blood volume based on the MTR of parenchyma and the MTR of tissue.

23. The MRI system of claim 22, wherein the processing component quantifies blood volume based on the following algorithm:

$$MTR_{par} = MTR_{tissue}(1 - BV/V_{par}),$$

where $MTR_{par}$ is the magnetization transfer ratio of parenchyma, $MTR_{tissue}$ is the magnetization transfer ratio of tissue, BV is the blood volume, and $V_{par}$ is a total parenchymal water volume.

24. The MRI system of claim 22, wherein the processing component is further programmed to:
determine a MTR of blood; and
quantify the parenchymal blood volume based on the MTR of parenchyma, the MTR of tissue and the MTR of blood.

25. The MRI system of claim 24, wherein the processing component quantifies blood volume based on the following algorithm:

$$MTR_{par} = MTR_{tissue} - (MTR_{tissue} - MTR_{blood})(BV/V_{par}),$$

where $MTR_{par}$ is the magnetization transfer ratio of parenchyma, $MTR_{tissue}$ is the magnetization transfer ratio of tissue, $MTR_{blood}$ is the magnetization transfer ratio of blood, BV is the blood volume, and $V_{par}$ is a total parenchymal water volume.

26. The MRI system of claim 21, wherein the processing component quantifies the blood volume for a MT effect in blood that is negligible or not negligible.

27. The MRI system of claim 21, wherein the processing component quantifies the blood volume based on MR signals obtained from imaging techniques including one or more of the following: spin echo, gradient echo, and stimulated echo.

28. The MRI system of claim 21 wherein the processing component that receives the MR signals quantifies blood volume change based on the MR signals.

29. The MRI system of claim 28, wherein the processing component is further programmed to:
determine a blood volume effect in parenchyma during physiological perturbations.

* * * * *